United States Patent [19]
Doherty

[11] Patent Number: 5,643,260
[45] Date of Patent: Jul. 1, 1997

[54] ORTHOPEDIC FIXATION SYSTEM

[75] Inventor: Brian J. Doherty, Atherton, Calif.

[73] Assignee: Smith & Nephew, Inc., Memphis, Tenn.

[21] Appl. No.: 388,350

[22] Filed: Feb. 14, 1995

[51] Int. Cl.$^6$ ............................................. A61B 17/56
[52] U.S. Cl. .............................. 606/61; 606/73; 606/60; 606/72
[58] Field of Search ..................... 606/61, 72, 73, 606/54, 59, 60; 623/17

[56] References Cited

U.S. PATENT DOCUMENTS

| | | |
|---|---|---|
| 4,171,012 | 10/1979 | Holmes . |
| 4,567,884 | 2/1986 | Edwards ........................ 606/61 |
| 4,826,377 | 5/1989 | Holmes . |
| 4,887,596 | 12/1989 | Sherman ........................ 606/61 |
| 5,176,678 | 1/1993 | Tsou . |
| 5,176,679 | 1/1993 | Lin . |
| 5,176,680 | 1/1993 | Vignaud et al. . |
| 5,306,275 | 4/1994 | Bryan . |
| 5,330,474 | 7/1994 | Lin ............................ 606/54 |
| 5,360,429 | 11/1994 | Jeanson et al. . |
| 5,387,212 | 2/1995 | Yuan et al. ..................... 606/61 |

OTHER PUBLICATIONS

Acromed product brochure (ISOLA Spinal System) (1993).
Ashman, R.B., et al. *TSRH Universal Spinal Instrumentation*, (1993), pp. 1–48; 58–63, 99–106, 134–141.
Rogozinski Spinal Rod System—Surgical Technique (U.S.A.).
Wisnewski, P. and Small, L., Rogozinski Spinal Rod System—"Biochemical Analysis" (U.S.A.).
Rogozinski Spinal Rod System—"System Design and Clinical Advantages" (U.S.A.).
Rogozinski, C. and Rogozinski, A., "The Rogozinski Spinal Rod System: A New Internal Rod Fixation of the Spine," 107–120 (1992) [reprint from *Spine* 6:107–120 (Jan. 1992)].
Danek Product bulletin: TSRH Spinal System—Shaping the Fuure of Spinal Instrumentation (1992).
White, A. Panjabi, M., *Clincal Biomechanics of the Spine*, 2nd Ed., pp. 590–596, 599–608, 613–615 (1990).
Smith & Nephew product bulletin—"Richards Scoliosis System—Short Technique.".
Rogozinski Spinal System—"Flexibility for Fit, Rigidity for Results."
Miami Moss product brochure (from Spine vol. 19 (Oct. 1994).
Sofamor Compact CD product brochure (U.S.A. 1993).
Synthes product brochure—Modular Spine System (U.S.A. 1991).

*Primary Examiner*—Michael Buiz
*Assistant Examiner*—Mark S. Leonardo
*Attorney, Agent, or Firm*—Pravel, Hewitt, Kimball & Krieger

[57] ABSTRACT

A rod-based orthopedic fixation system, in particular a spinal fixation system, comprising orthopedic fasteners which utilize a novel set screw system for securing a cylindrical longitudinal member or orthopedic fixation rod to the fastener. Also disclosed are transverse extension devices useful for connecting a spinal fixation rod to an orthopedic fastener to minimize rod contouring in both the frontal and sagittal planes.

38 Claims, 12 Drawing Sheets

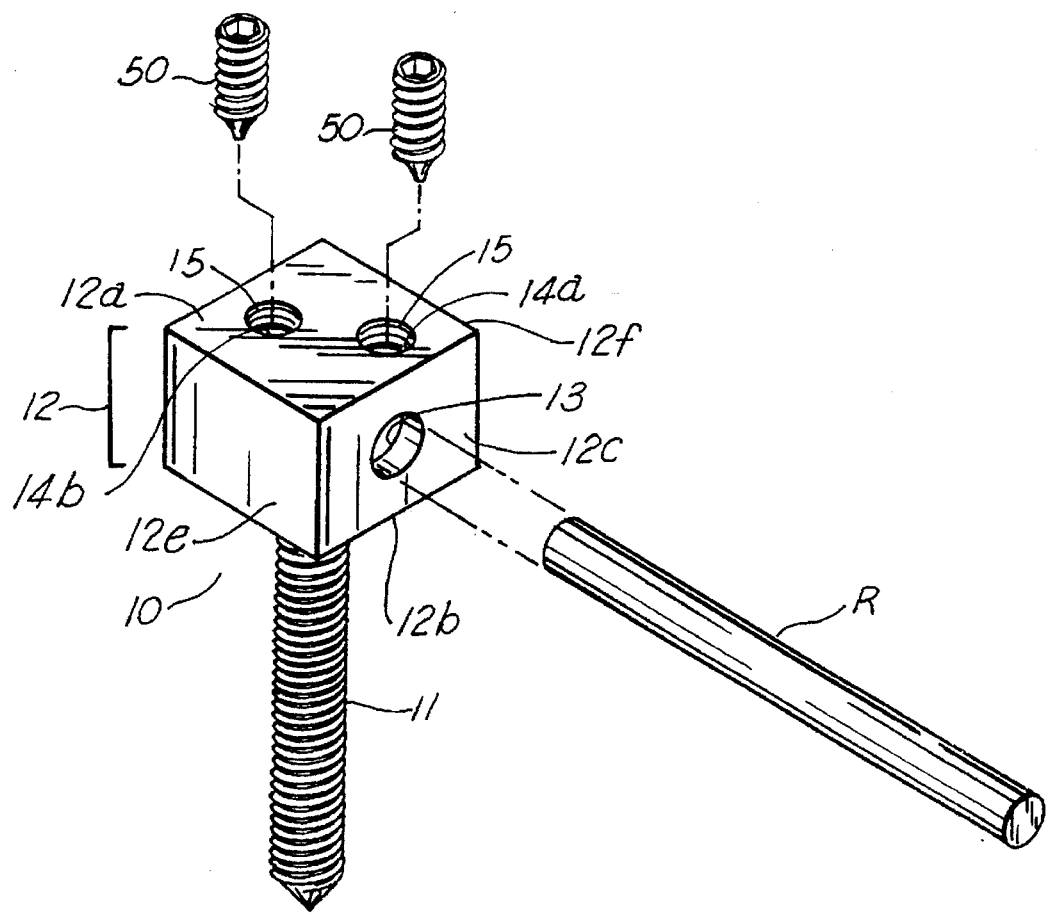
FIG. 1
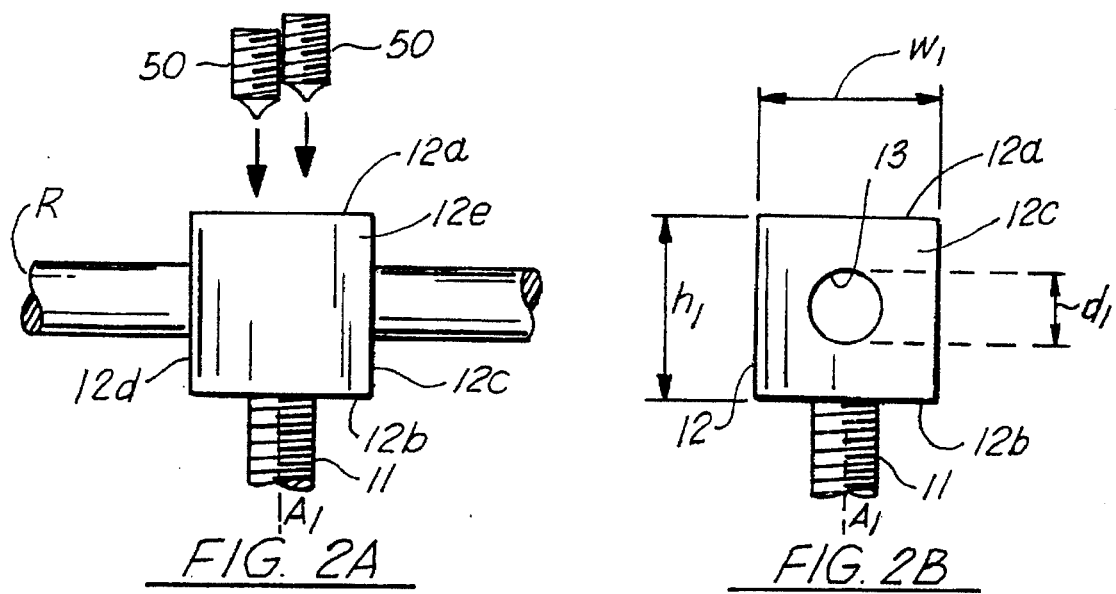
FIG. 2A
FIG. 2B

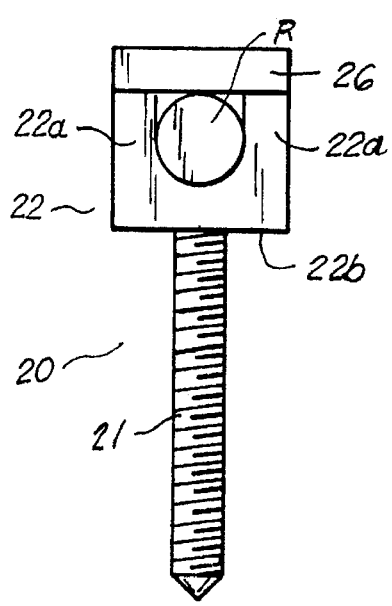 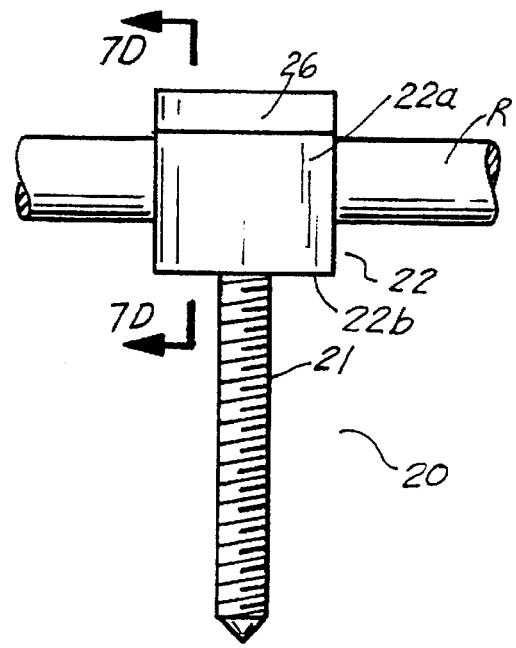
FIG. 7A    FIG. 7B
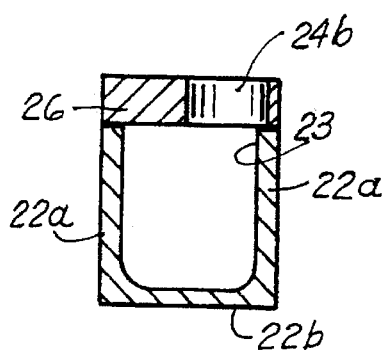 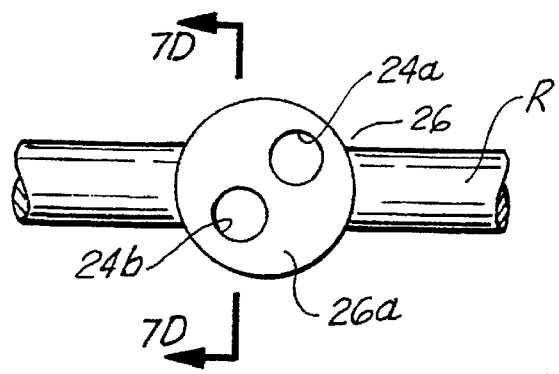
FIG. 7D.    FIG. 7C
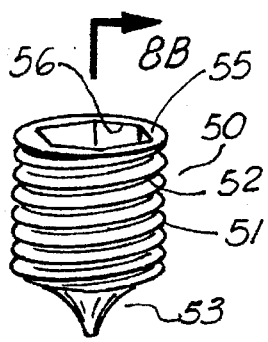 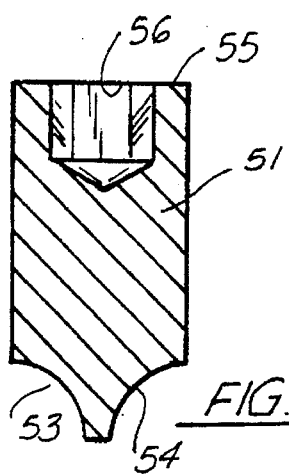 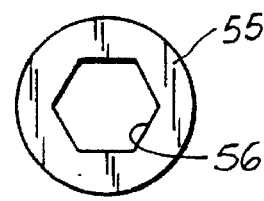
FIG. 8A    FIG. 8B    FIG. 8C

ORTHOPEDIC FIXATION SYSTEM

BACKGROUND OF INVENTION

1. Field of Invention

The present invention is related to components useful in securing internal and external orthopedic fixation devices, particularly rod-based internal spinal fixation systems.

2. Description of Related Art

Internal fixation of the spine has been important in the surgical management of a variety of spinal disorders. The vast majority of implants for this purpose employ a longitudinal stabilizing device (either a rod or a plate) which is attached to the spine by means of hooks or screws. Hooks typically engage the spine by their position of insertion around the spinal lamina or transverse process. Screws engage the spine by affixing directly to the bone of the anterior vertebral body or through the pedicles posteriorly. An additional option in the cervical spine is the insertion of screws into the lateral masses of the vertebrae. Attachment of the hook and/or screw to the longitudinal fixation device is an important linkage in this construct.

The spinal surgeon would ideally wish to have a means to achieve an extremely rigid stabilization of the hook or the screw to the longitudinal fixation device. There are also significant advantages to coupling systems which allow the hook or screw to be affixed to the longitudinal fixation device through a variety of different angles.

One of the original devices for internal fixation of the spine is the Harrington rod. This device consists of a stainless steel rod to which is affixed hooks designed to be placed beneath the laminae of the vertebrae posteriorly. A single hook is attached to the rod inferiorly by means of a hole through the top of the hook into which the rod rests. The second hook also contains such a hole which engages the rod in a ratchet-like mechanism to allow the application of distraction. Numerous spinal fixation devices since the initial development of the Harrington rod have employed the technique of threading the rod through a hole in the screw or hook. Refinements in this technique includes implants such as the Cotrel-Dubosset in which multiple hooks and/or screws can be inserted along the length of a single rod. In the case of the Cotrel-Dubosset implant, this is accomplished by means of small flat-headed locking screws which transfix the cannulated hook and directly engage the rod by single point-fixation. Hooks used in the Cotrel-Dubosset system are fixed to the rods via the means of these one, two, or three small locking screws.

On some occasions (particularly during surgery for spinal deformity), it is not possible to have such closed cannulated hook and screw heads, and threading a rod through multiple hooks or screws can be difficult or impossible. To overcome this, the Cotrel-Dubosset implant system uses an "open" screw head which allows the rod to be placed into the screw head or hook head from above. In the case of the Cotrel-Dubosset device, this is accomplished by means of a circular insert which fits into the semi-circular screw head and subsequently accepts locking screws identical to those used in the closed hook and screw systems. In both "open" and "closed" hooks and screws, the rod nonetheless must be contoured to lie fairly precisely within the screw head or hook fitting in order to allow stable fixation to the rod.

A similar design is found in Acromed's ISOLA system. In this system, "open" and "closed" headed hooks and screws are also available. The "closed" head design allows passage of the rod through the hole in the screw or hook head which is then fixed in place by a single, vertically-oriented locking screw. Open head designs for the ISOLA system involve a sliding "top" to the screw or hook head which contains the locking screw. The sliding top of the screw or hook head snaps into position and allows placement of the single locking screw for fixation of the rod. This system also requires contouring of the rod through the screw head in every application.

Another approach applied in situations where threading the rod through multiple screw/hook heads is too difficult or impossible involves designs in which the rod passes adjacent to the screw or hook. Examples of this would be the Texas Scottish Rite Instrumentation (TSRI) in which the rod is fixed to the screw by the shortening action on a transverse linkage effected by tightening a bolt. A top tightening version of this instrumentation system involves an obliquely-placed top loading single locking screw. The TSRI system allows for rotation of the hook or screw in the sagittal plane prior to tightening. This increased flexibility allows considerably decreased operative time and effort in accurately contouring the rod since the rod can be rigidly attached to screws at various angles in this sagittal plane without contouring. However, when implanting the system, it is extremely important that the spinal fixation rod be properly seated within the groove of each eyebolt prior to tightening to ensure secure three-point fixation upon the rod once tightening is performed. Further, to ensure a secure grip, the bolt must be tightened down to a minimum of 150 in-lb to reduce the chance of nut loosening.

It is therefore desirable to have an internal spinal fixation device suitable for rod-based fixation in both the anterior and posterior spinal regions which further includes the following attributes:

(1) a simple, modular design employing interchangeable components;

(2) requires few components;

(3) requires only minimal or no rod contouring by allowing for variable angulation and adjustment of the screw or hook head in both the sagittal and frontal planes;

(4) contains a locking system that securely engages the rod to prevent slippage; and (5) requires no special training to use.

SUMMARY OF THE INVENTION

The present invention is directed to orthopedic components particularly useful in rod-based internal spinal fixation systems used anteriorly and posteriorly in the thoracic, lumbar, and sacral regions of the spine. Specifically, the inventive system includes both open head and closed head orthopedic fasteners such as vertebral screws and hooks, for example, which employ a novel locking system for securing a longitudinal rod or member within the fastener head. The closed head embodiment contains a transverse bore through which a longitudinal rod or member may be inserted. The open head design allows for the longitudinal rod or member to drop onto a channel contained within the head; afterwards a lid is locked onto the head to enclose the rod or member therein. On the top end of the closed head fastener, or the lid of the open head fastener, are a pair of holes communicating therethrough with the transverse bore. The holes are positioned such that the rod or longitudinal member is aligned between each of the holes.

The inventive locking system comprises a pair of novel set screws, each of which is inserted through each of the pair of holes located on the fastener head, or lid in the case of the open head embodiment. Each of the set screws preferably includes a concave-shaped tip configured to secure a longitudinal rod or member therebetween within the fastener head. Specifically, the inner concaved surface of each screw tip has substantially the same radius as the longitudinal member or rod it is engaging. Once the screws are tightened down within the fastener head, the longitudinal rod or member is securely clasped between the lower tips of the two screws resulting in a three-point shear clamp grip. No special alignment of the rod within the head is required. In fact, the system is self-aligning in that the rod (or member) is seated properly as the set screws are tightened down.

When used in other orthopedic applications (both internal and external) employing a cylindrically shaped longitudinal device, the inventive locking mechanism comprises a pair of set screws, configured as previously described, and a housing component similar to the head of the inventive orthopedic fastener. Like the inventive fasteners described herein, the housing component may be of a "closed" design and contain a transverse bore. Similarly, the housing component may be an "open" design, further including a lid for attachment thereon. And like the inventive fastener heads, the housing component comprises a pair of holes (either on the component itself in the "closed" design or on the lid in the "open" design) positioned perpendicular to, and communicating with, the transverse bore of the housing component. The holes are oriented such that the longitudinal device is aligned between each of the holes.

Another aspect of the inventive system is directed to a transverse extension device suitable for connecting orthopedic screws or hooks, in particular those engaged in the spine, to a longitudinal member such as a spinal fixation rod. Preferably, the transverse extension device is used in combination with the inventive orthopedic fasteners described herein, thereby requiring fewer components since the transverse connector can be used anywhere along the area of fixation. The inventive transverse extension device not only allows the screws or hooks to be offset from the rod in the frontal plane, but it is also fully rotatable to allow for sagittal plane angulation of the screw or hook. Consequently, the inventive transverse extension device allows for minimal rod contouring during rod placement onto the spine. Eliminating, or at least minimizing, the amount of rod contouring is particularly desirable in treating scoliosis, for example, where the spine is extremely curved, or in the treatment of other spinal conditions where the placement of spinal screws or hooks requires aggressive contouring of the rod, absent the presence of any kind of transverse extension system.

The inventive transverse extension device includes a transverse connector having a head and substantially cylindrical longitudinal member. In the preferred embodiment, the head of the connector is designed very similarly to the inventive open head and closed head fasteners described herein and further incorporates the novel set screw system for securing a longitudinal rod within the connector head. Preferably, the inventive transverse connector is designed for use in combination with the inventive orthopedic fasteners described herein as part of a spinal fixation kit, for example. Here, the longitudinal member of the transverse connector has substantially the same diameter as the spinal fixation rod and is configured for insertion into the transverse bore of the inventive fastener head. Such a combination provides many advantages over prior art rod-based internal spinal fixation systems. One advantage is that fewer components are required since, for example, the same transverse connector can be used anywhere along the fixation area, and the same set screws may be used for both the orthopedic fastener and the transverse extension device. Similarly, no extra components are required to link the connector to the fastener head since the longitudinal member of the transverse connector has substantially the same diameter as a spinal fixation rod. Furthermore, all of the components are assembled from above and are self-aligning; the components are assembled in a single motion and secured immediately upon insertion; the system requires no special tools; and no special training is required on the part of the surgeon. The inventive system is also less expensive in that only conventional implant materials are required, the design is simple and thus requires no complex machinery to manufacture, and the same transverse connectors and set screw systems may be used throughout as discussed above, thus reducing inventory. Moreover, the head designs and set screw system of the present invention can be applied to virtually any type of conventional orthopedic fastener or housing device used in both internal and external orthopedic applications.

BRIEF DESCRIPTION OF THE DRAWINGS

FIG. 1 is an exploded perspective view of the closed head screw, set screw system, and a rod.

FIG. 2A is a side elevation view of the closed head screw embodiment housing a rod.

FIG. 2B is a front elevation view of the closed head screw.

FIG. 7A is a front elevation view of the open head screw embodiment housing a rod.

FIG. 7B is a side elevation view of the open head screw embodiment illustrated in FIG. 7A.

FIG. 7C is a top plan view of the open head screw embodiment illustrated FIG. 7A.

FIG. 7D is a cross-sectional view of the open head screw embodiment taken along lines 7D—7D of FIGS. 7B and 7C.

FIG. 8A is a perspective view of the set screw.

FIG. 8B is a cross-sectional side view of the set screw taken along lines 8B—8B of FIG. 8A.

FIG. 8C is a top plan view of the set screw.

DETAILED DESCRIPTION OF THE PREFERRED EMBODIMENTS

Figure 2C:
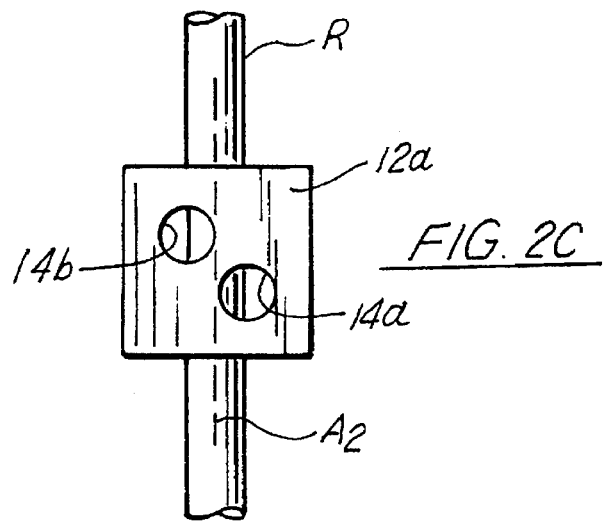
FIG. 2C is a top plan view of the closed head screw embodiment.
Figure 3A:
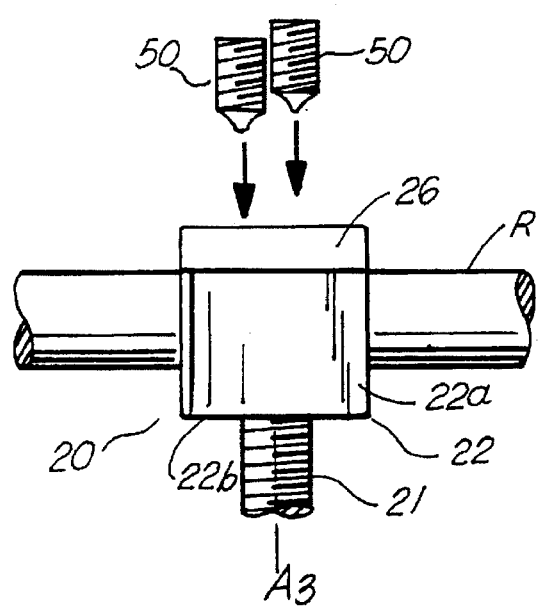
FIG. 3A is a side elevation view of the open head screw embodiment housing a rod.
Figure 3B:
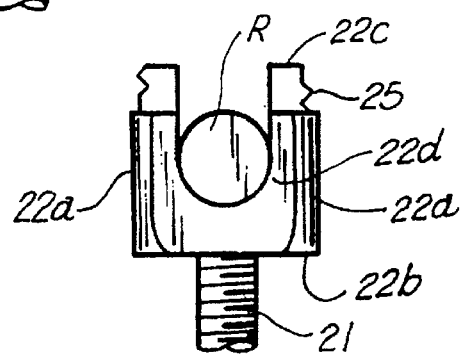
FIG. 3B is a front elevation view of the open head screw embodiment housing a rod.
Figure 3C:
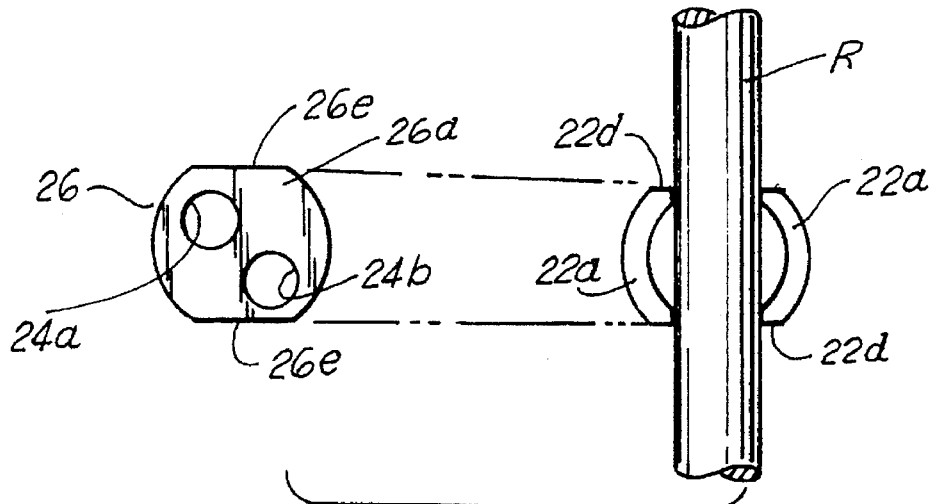
FIG. 3C is a top plan view of the open head screw embodiment.

The present invention, in certain embodiments, is related to novel orthopedic bone fasteners which utilize a novel set screw system for securing the fastener to a longitudinal member such as a spinal fixation rod, for example. For ease of explanation, the present invention is described with reference to screws and hooks used in rod-based internal spinal fixation, most preferably anterior and posterior fixation in the thoracic, lumbar, and sacral regions of the spine. However, it is contemplated that one of ordinary skill in the art, having the benefit of this invention's teachings and suggestions, will be able to employ the inventive devices in other orthopedic applications requiring the fixation of an orthopedic fastener to a rod, for example. Such orthopedic applications may include, but are not limited to, external spinal fixation, external fixation for various long bone fractures utilizing rods, and intramedullary rods used to stabilize fractured femurs, for example.

Referring now to the figures, the inventive screws and hooks include "closed head" and "open head" embodiments, both of which utilize a novel set screw system designed to engage and securely maintain a longitudinal member, such as a spinal fixation rod, within the head for better spinal stabilization. FIGS. 1 and 2A–C illustrate the closed head embodiment as a typical screw used in spinal fixation, such as a pedicle screw, for example. The screw (10) comprises an upper head (12) and a threaded shaft (11) for engaging a vertebral pedicle posteriorly, for example, or a cancellous vertebral body anteriorly, for example. The screw head (12) comprises a lower end (12b) integral with the shaft (11) and an upper end (12a). A preferred height ($h_1$) and width ($w_1$) of the screw head for use in spinal fixation is generally that of conventional pedicle screws, typically about 0.50 inches. While the screw head (12) may be cylindrically shaped, the most preferred embodiment is box- or rectangularly-shaped and comprises at least four substantially flat side walls (12c–f) integral with the upper (12a) and lower (12b) ends of the head, as illustrated in FIGS. 1 and 2A–C. Contained within the screw head is a transverse bore (13) for housing a longitudinal member such as a spinal rod (R), for example, wherein the bore (i.e. the longitudinal axis ($A_2$)) is perpendicular to the longitudinal axis ($A_1$) of the lower threaded shaft (11) and communicates between two parallel sides (12c, 12d). The transverse bore (13) may be of a variety of appropriate shapes to accommodate a particular longitudinal member; however, in the most preferred embodiment it is substantially cylindrical to accommodate a substantially cylindrical longitudinal member, such as a spinal fixation rod (R), for example. The size or diameter ($d_1$) of the transverse bore (13) should be just large enough so that the desired longitudinal member, most preferably a spinal rod, may be easily inserted through the bore.

While the most preferred embodiment of the inventive screw comprises a box- or rectangularly-shaped head having four sides, the head (12) may have a greater number of sides, provided at least two side walls are parallel to one another for containing the transverse bore (13). Thus, a screw head having a hexagon or octagon shape, for example, would be suitable, as well. Furthermore, this latter embodiment comprising a head having substantially flat parallel side walls is especially preferred over an embodiment having a cylindrically shaped head in cases where the screw is used in combination with the inventive transverse device, as discussed in more detail below.

The upper end (12a) of the screw head further includes a pair of holes (14a, 14b) communicating with, and perpendicular to, the longitudinal axis ($A_2$) of the transverse bore (13) or rod (R). Preferably, the pair of holes (14a, 14b) are staggered and orientated such that a longitudinal member (for example a spinal fixation rod (R), as shown in FIGS. 1 and 2A–C) positioned within the transverse bore (13) is aligned between each of the two holes (14a, 14b).

Figure 10A:
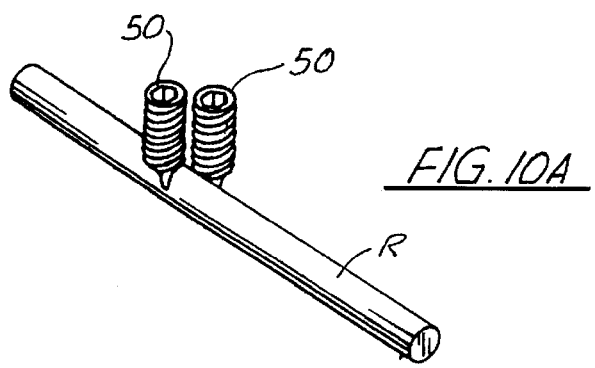
FIG. 10A is a perspective view of the set screw system engaging a rod.
Figures 10B, 10C:
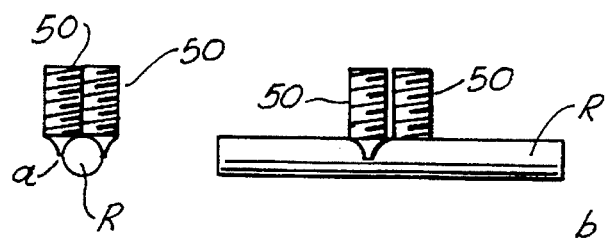
FIG. 10B is a side elevation view of the set screw system as shown in FIG. 10A.
FIG. 10C is a front elevation view of the set screw system engaging a rod.
Figure 10D:
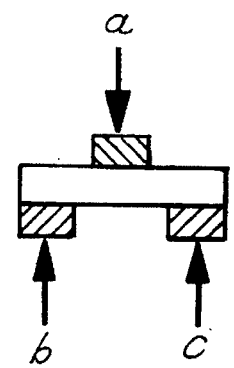
FIG. 10D is a view of a general three-point clamp mechanism.
Figure 10E:
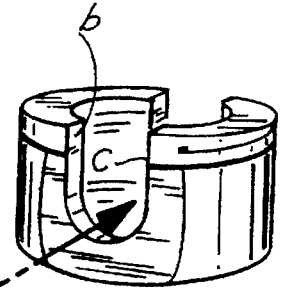
FIG. 10E is a perspective view of the open-head housing component.

Engaged within each of the two holes (14a, 14b) is a set screw (50), as shown in FIGS. 1, 2A–C, and 8/a–C, for example. In the most preferred embodiment, the set screw (50) comprises a substantially cylindrical upper body (51), preferably containing threads (52), which tapers downward into a lower tip (53). The upper body (51) preferably has a diameter which is substantially the same as the diameter of conventional spinal fixation rods, typically about 4.5 mm to about 6 mm. Likewise, when used in other orthopedic applications, the upper body of the set screw has a diameter that is substantially equal to the typical diameter of the particular type of longitudinal member employed. The lower tip (53) contains a concave outer surface (54) which is configured to complement the cylindrical surface of a longitudinal member such as a spinal fixation rod, for example. Preferably, the concave surface (54) has substantially the same radius as the longitudinal member or rod. A conventional orthopedic screw driver (not shown) may be used to engage the set screw (50) into the screw head (12) by inserting the screw driver into a bore (56) located on the top surface (55) of the set screw. By tightening the set screw (50) down within the screw head (12) containing the longitudinal member, a three-point shear clamp grip onto the longitudinal member positioned therebetween is achieved. Specifically, the combination of the two set screws form a single central force point (a) while the inner sides (b,c) of the transverse bore or channel each serve as one of the remaining two force points, as illustrated in FIGS. 10C–E (FIG. 10D illustrates a general 3-point clamp mechanism). In addition, proper seating of the longitudinal member within the screw head (12) is achieved as both set screws are tightened down. Consequently, proper alignment of the longitudinal member or rod within the screw head prior to insertion of the set screws is not necessary for proper fixation.

In order to secure the set screws (50) within the screw head (12), a locking mechanism is particularly desireable. Appropriate modifications of the set screw (50) to achieve a desired locking screw mechanism may be employed which are obvious to one of ordinary skill in the art having the benefit of this invention's teachings and suggestions. A particularly preferred locking mechanism is well known to those of ordinary skill in the art under the trademark SPIRALOCK (the trademark SPIRALOCK is owned by Horace D. Holmes who is the inventor of the SPIRALOCK design and its various embodiments, as described and claimed in his U.S. patents, which include, for example, U.S. Pat. Nos. 4,171,012 and 4,826,377, for example). The SPIRALOCK locking design in general comprises female threads of a hole or nut which have a different shape than what would be complementary to the conventional male threads of the threaded fastener, such that the male threads are wedged with relatively large force against the female threads upon engagement of the fastener within the uniquely threaded hole or nut. Thus, the locking action occurs as the crests of the male thread are wedged as a "knife edge" against ramps formed by the female thread, as described and illustrated in U.S. Pat. Nos. 4,171,012 and 4,826,377, which are incorporated in their entirety by reference herein. As applied to the present invention, the female threads (15) of the set screw holes (14a, 14b) possess the ramp-like SPIRALOCK configuration while the locking set screw (50) possesses conventionally shaped male threads (52).

Figure 11A:
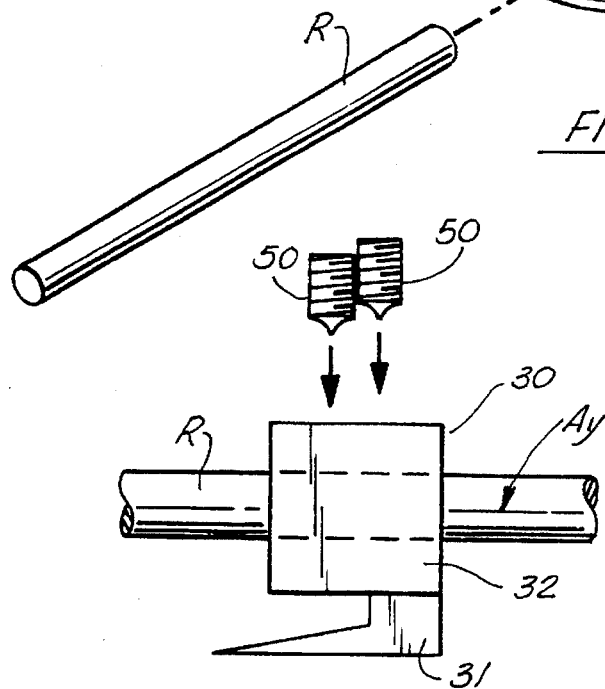
FIG. 11A is a side elevation view of a closed head hook embodiment housing a rod.
Figure 11B:
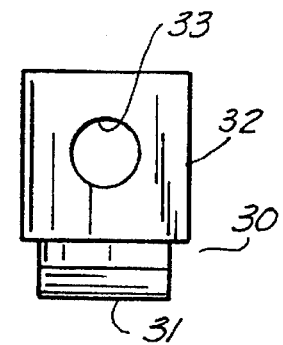
FIG. 11B is a front elevation view of the closed head hook embodiment of FIG. 11A.
Figure 12A:
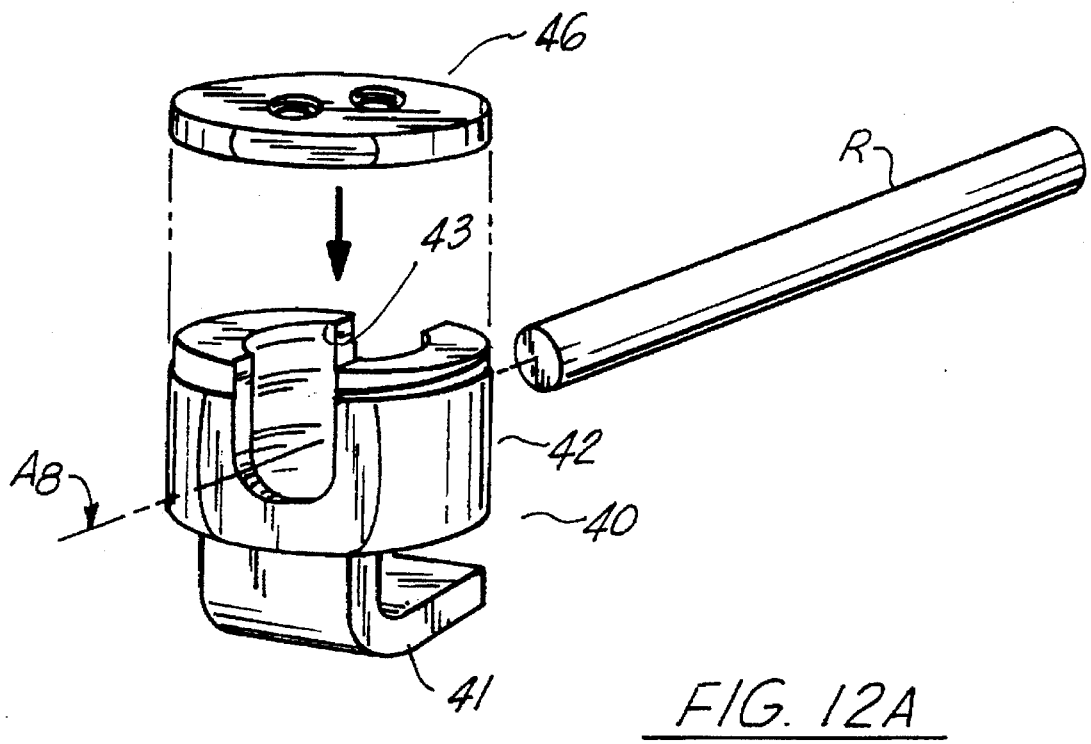
FIG. 12A is an exploded perspective view of a first embodiment of the open head hook.
Figure 12B:
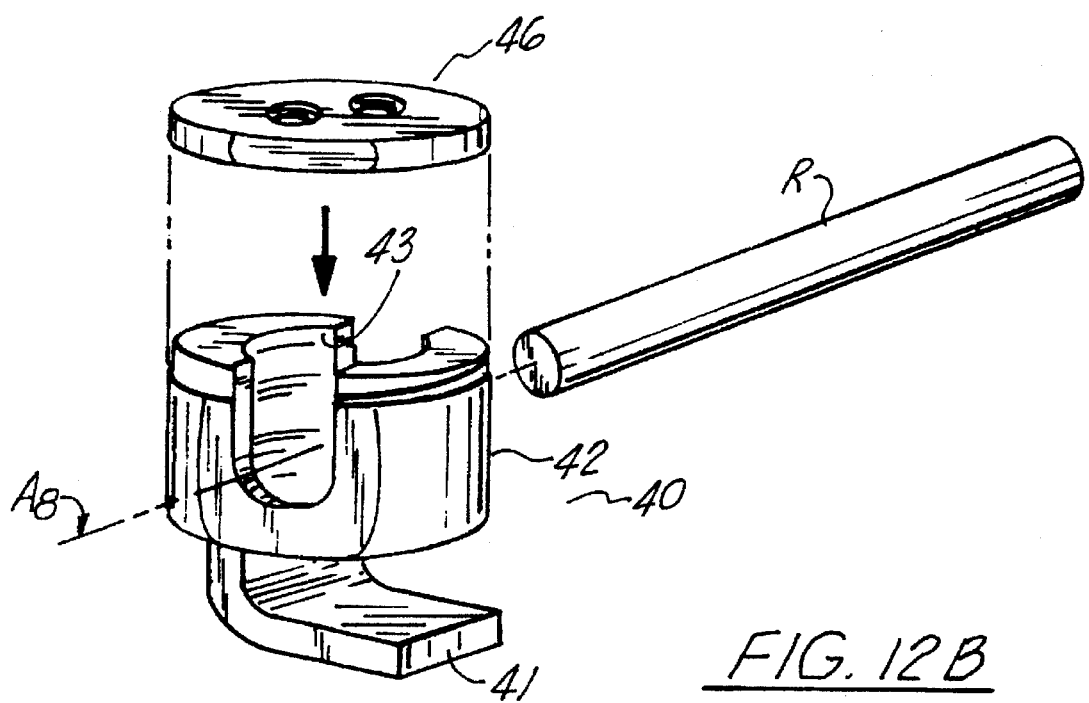
FIG. 12B is an exploded perspective view of a second embodiment of the open head hook.

The closed head design described above for the screw (10) can also be applied to spinal hooks, as illustrated in FIG. 11A. In one aspect of the present invention, the spinal hook (30) comprises a lower engaging means (31) and is designed to engage the vertebra posteriorly around the transverse process or spinal lamina, for example. FIGS. 11A–B illustrate a conventional hook-shaped engaging means commonly found in many spinal hooks. However, while not illustrated in the figures, the engaging means may have any variety of different shapes and lengths, and employ different engaging mechanisms for example, in order to accommodate a specific vertebrae. Furthermore, the engaging means may be positioned parallel to the longitudinal axis ($A_7$) of the transverse bore of the head, as shown in FIGS. 11A–B, or perpendicular to the longitudinal axis ($A_7$) of the transverse bore, as shown in FIG. 12B (FIGS. 12A–B illustrate the open-head hook embodiments, described in more detail below). The closed head (32) of the hook is identical to that described for the closed head screw (10) and preferably employs the same set screw system.

In the "open" head design for the screw, as shown in FIGS. 3A–C and 4A–C, the inventive screw (20) comprises an upper head (22) and a lower threaded shaft (21) extending therefrom for engaging a vertebra as described above for the "closed" head screw (10). The head (22) comprises a lower end (22b) integral with the lower threaded shaft, and two parallel side walls (22a) integral with the lower end (22b). The head further includes an upper end (22c) positioned opposite the lower end and integral with the two parallel side walls. Also integral with the two parallel side walls are two U-shaped side walls (22d) (only one U-shaped side wall is shown) positioned parallel to one another and perpendicular to the two parallel side walls (22a). For reasons discussed in more detail below, preferably one, more preferably both, of the two U-shaped side walls (22d) are substantially flat and include a roughened or knurled surface, as indicated by the shading. The head further includes a longitudinal channel or bore (23) communicating between the two parallel side walls (22a) and two U-shaped side walls (22d). The channel (23) is also positioned perpendicular to the longitudinal axis ($A_3$) of the threaded shaft (21). This open head embodiment (20) may be preferred over the closed head embodiment (10) in cases where it is difficult or impossible to thread a rod through multiple screws.

Figures 4A, 4B, 4C:
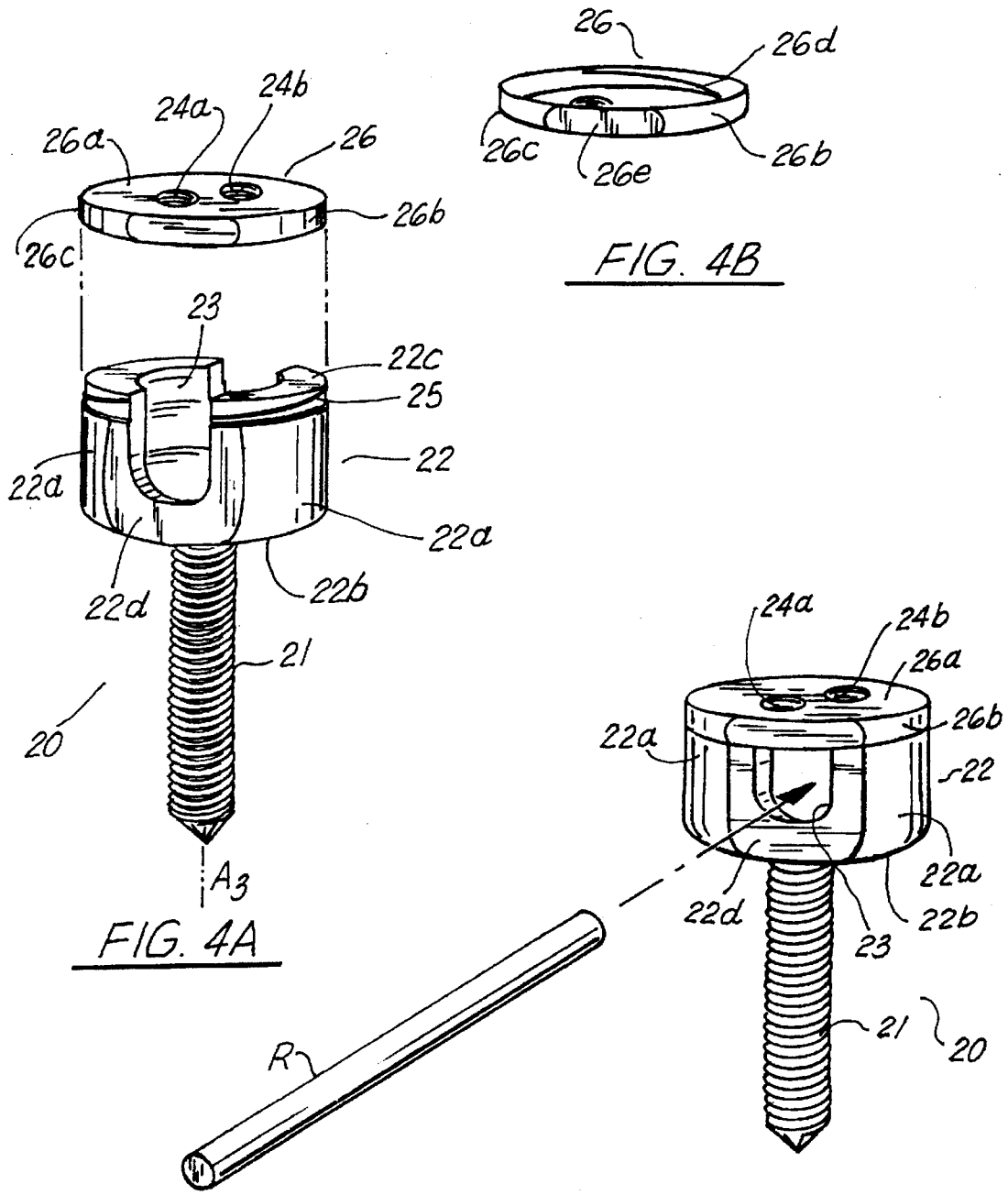
FIG. 4A is an exploded perspective view of the open head screw embodiment.
FIG. 4B is a perspective view of the inverted lid of the open-head screw embodiment illustrated in FIG. 4A.
FIG. 4C is a perspective view of the assembled open head screw embodiment.

Once the rod or longitudinal member is placed within the channel (23), a lid (26) is attached to the upper end (22c) of the head (22), as shown in FIGS. 4A–C, for example. The lid (26) may be designed to snap onto the upper end (22c). More preferably, however, the lid comprises a top portion (26a) and a rim (26b) integral with, and extending perpendicular to, the outer edge (26c) of the top portion, as shown in FIGS. 4A–B. As illustrated more clearly in FIGS. 3B and 4A–4B, the rim includes an inner threaded surface (26d) which is substantially circular and configured to engage a threaded rim (25) located on the outer surfaces of the head. Most preferably, the inner threaded surface (26d) of the lid and the threaded rim (25) of the screw head are designed such that upon about a one quarter turn of the lid (26) onto the head (22), the lid locks into place in a similar fashion to conventional child-resistant medicine caps, for example. The rim (26b) of the lid is preferably of sufficient thickness such that it may include on its outer surface at least two flat portions (26e) positioned parallel to one another for alignment with the U-shaped side walls (22d) of the head, as shown in FIGS. 3C and 4A–C.

Like the upper end (12a) of the closed head embodiment (10), the top portion (26a) of the lid further includes a pair of holes (24a, 24b) communicating therethrough, and perpendicular to, the channel or bore (23). Preferably, the two holes (24a, 24b) are staggered and oriented such that a longitudinal member, when placed within the channel (23), is aligned between each of these two holes (24a, 24b), as shown in FIGS. 7A–7D, for example. Positioned within each of the two holes (24a, 24b) is the identical set screw (50) as described previously for the closed head screw embodiment.

The open head design described above for the screw (20) can also be applied to spinal hooks, as illustrated in FIGS. 12A–B. The spinal hook (40) comprises a lower engaging means (41) designed to engage the vertebra posteriorly around the transverse process or spinal lamina, for example. The engaging means (41) may be parallel to the longitudinal axis ($A_8$) of the transverse channel (or bore). As for the closed head hook embodiment (30) described above, the engaging means may also have any variety of different shapes and lengths, and employ different engaging mechanisms for example, to accommodate a specific vertebrae, and thus, is not limited in scope by the figures. Furthermore, the open head (42) of the hook is identical to the head (22) described for the open head screw (20), and thus includes the same lid (46) design and set screw system as described above.

The screws and hooks described herein may be engaged into the vertebra for internal rod-based spinal fixation, preferably in the thoracic, lumbar, and sacral spinal regions, both anteriorly and posteriorly, by conventional means well known by those of ordinarily skill in the art. While the closed head embodiments are generally stronger and easier to manufacture, the inventive open head design described herein may nonetheless be preferred when it is extremely difficult or impossible to thread a rod into a plurality of such fasteners.

In internal spinal fixation especially, there are often instances when due to the severe curvature of the spine in the frontal plane, the orthopedic fasteners are aligned in a nonlinear fashion. In other words, the longitudinal axes of the spinal fixation rod and the fastener are not aligned, thus requiring major contouring of the metal rod in order to secure the rod to the fastener. Similarly, the orthopedic fasteners may be positioned within the vertebrae such that the transverse bores of the fastener head do not share the same axis as the rod in the sagittal plane, thereby requiring in some cases significant contouring of the rod in this plane, as well. Not only is it generally very difficult to contour a spinal fixation rod to a significant degree, but such contouring may cause deleterious stresses on the rod and undue strain on the spine, thereby severely compromising fixation. Consequently, attachment of a transverse extension device of sufficient length to both the spinal rod and the fastener head eliminates the need for major rod contouring in the frontal plane. Moreover, the inventive transverse extension device allows for variable angulation of the rod in the sagittal plane, thereby minimizing rod contouring in this plane, as well.

Figure 5A:
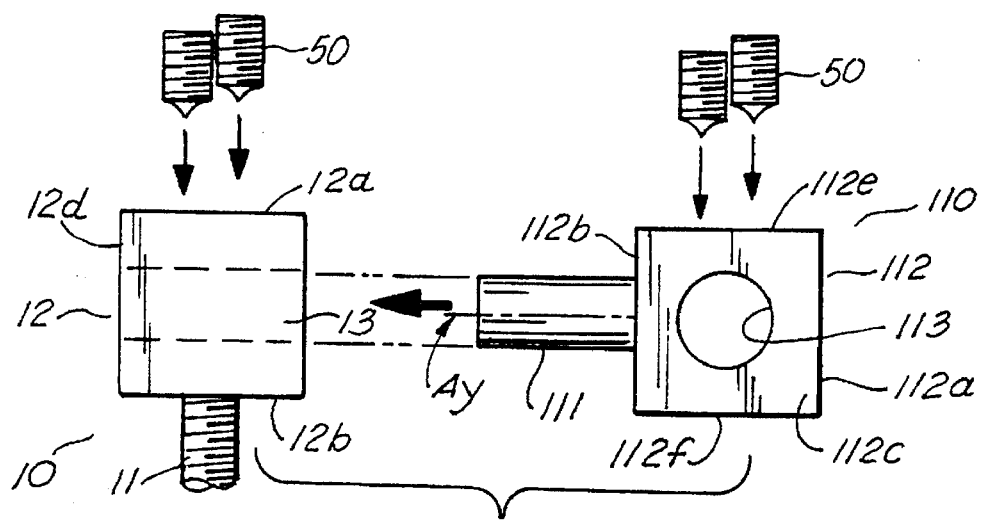
FIG. 5A is an exploded side elevation view of the screw and closed head transverse extension device assembly.
Figure 5B:
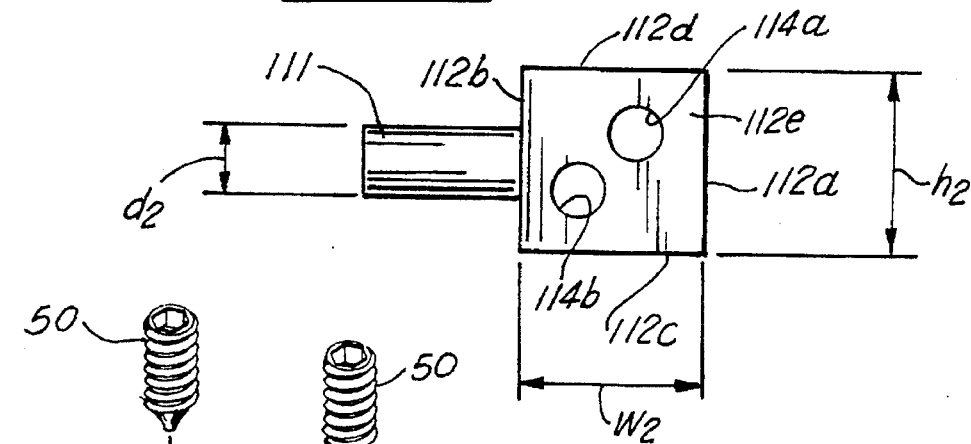
FIG. 5B is a top plan view of the transverse extension device illustrated in FIG. 5A.
Figure 9A:
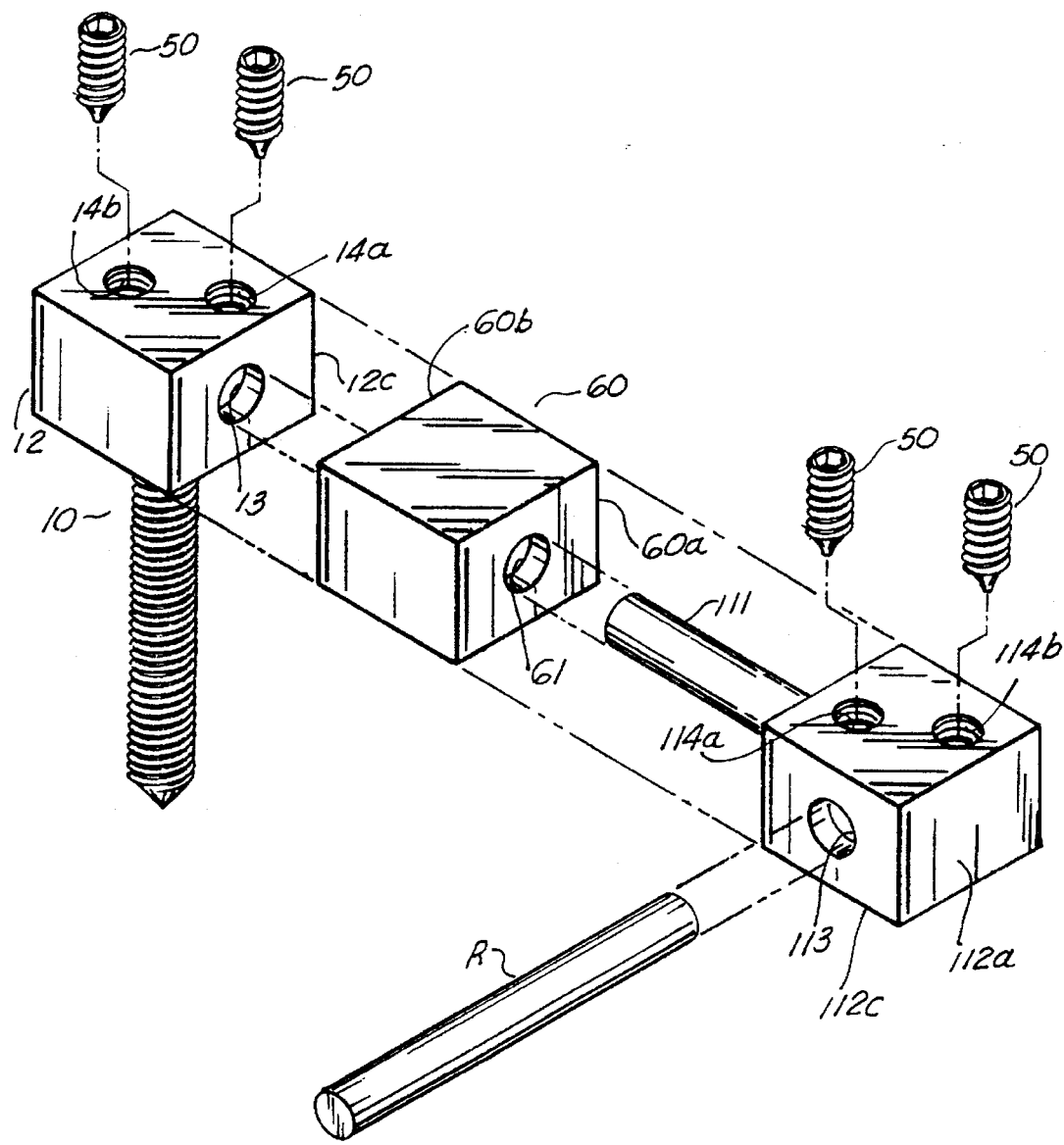
FIG. 9A is an exploded perspective view of the closed head screw, set screws, spacer, closed head transverse extension device, and rod assembly.

Referring now to FIGS. 5A-B and 9A, the inventive transverse extension device comprises a transverse connector (110) having a head (112) and a longitudinal member (111) integral with, and extending from, a side wall (112b) of the head. Most preferably, the longitudinal member (111) is cylindrically shaped and has approximately the same diameter ($d_2$) as the spinal fixation rod employed so that it may be easily inserted through the bore of an orthopedic fastener head, most preferably the inventive orthopedic fasteners described herein.

In the most preferred embodiment, the closed head design of the transverse extension device is very similar to that of the closed head fasteners described above, as shown in FIGS. 1 and 2A-C, for example. As discussed in more detail below, the main difference between the transverse connector head design and the orthopedic head design of the present invention is in the position of the pair of holes used to engage the set screws. Specifically, the closed head (112), which may be cylindrically shaped, is most preferably box- or rectangularly-shaped. Contained within the head (112) is a transverse bore (113) for housing a longitudinal member, wherein the bore (113) extends perpendicular to the longitudinal axis ($A_4$) of the longitudinal member (111) and communicates between two parallel side walls (112c, 112d). The transverse bore (113) may be of a variety of appropriate shapes to accommodate a particular longitudinal member; however, in the most preferred embodiment, the transverse bore (113) is substantially cylindrical to house a substantially cylindrical longitudinal member, such as a spinal fixation rod (R) or the longitudinal member of another transverse connector, for example. The size or diameter of the bore (113) should be just large enough so that the desired longitudinal member may be easily inserted through it. Further, while the box-shape head is the most preferred embodiment (as shown in FIGS. 5A-B and 9A-C), the transverse connector head (112) may have a greater number of side walls, provided at least two side walls are parallel to one another for containing the transverse bore (113), as discussed above for the closed head orthopedic fasteners. However, the head could be substantially cylindrical, as well, although this embodiment would not be preferred for use with the inventive orthopedic fasteners described herein.

Figure 5C:
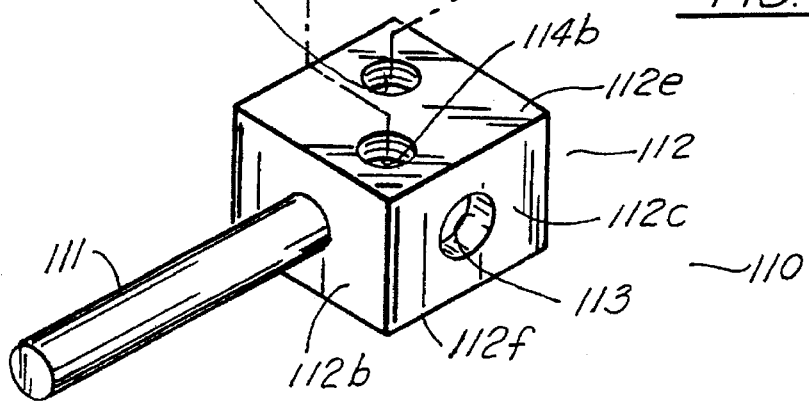
FIG. 5C is an exploded perspective view of the closed head transverse extension device.

The outer surface of the side wall (112b) which is integral with the longitudinal member (111) and parallel to the transverse bore (113) is preferably substantially flat and roughened, as illustrated by the shaded area in FIG. 5C. Preferably, the outer surface of the side wall (112b) is in direct contact with the roughened surface (12c) of the adjacent fastener head or a spacer, as indicated by shading in some of the figures (e.g. FIG. 9A). Providing such a roughened or knurled texture to these adjacent surfaces serves to increase the frictional forces therebetween, thereby minimizing any sliding motion between the components, resulting in a more secure fixation of the spine. The outer surface of the two parallel side walls (112c, 112D) may also be roughened or knurled as shown by the shading in FIGS. 5A and 5C, for example, which is desireable in cases where the connector is attached to a second transverse connector. The preferred height ($h_2$) and width ($w_2$) of the connector head (112) is about 0.50 inches.

The head of the transverse connector, like that of the inventive orthopedic fastener, further includes a pair of holes (114a, 114b) communicating with the transverse bore (113). The pair of holes are not, however, positioned coaxially with the longitudinal member, but instead are positioned on a side parallel to the longitudinal axis ($A_4$) of the longitudinal member (111). Thus, the pair of holes are aligned perpendicular to the longitudinal axis ($A_4$) of the longitudinal member to allow the surgeon top access to the connector head and set screw system for easier assembly. Further, the two holes (114a, 114b) are preferably staggered and oriented such that the rod (R) or another longitudinal member, for example, is aligned between each of the two holes. Moreover, the same inventive set screws (50) as described above for the inventive orthopedic fasteners are most preferred for securing the rod or other substantially cylindrical longitudinal member, for example, within the head (112) of the transverse connector. However, the head (112) could be modified to accommodate other conventional locking mechanisms known by those of ordinary skill in the art.

Figure 6A:
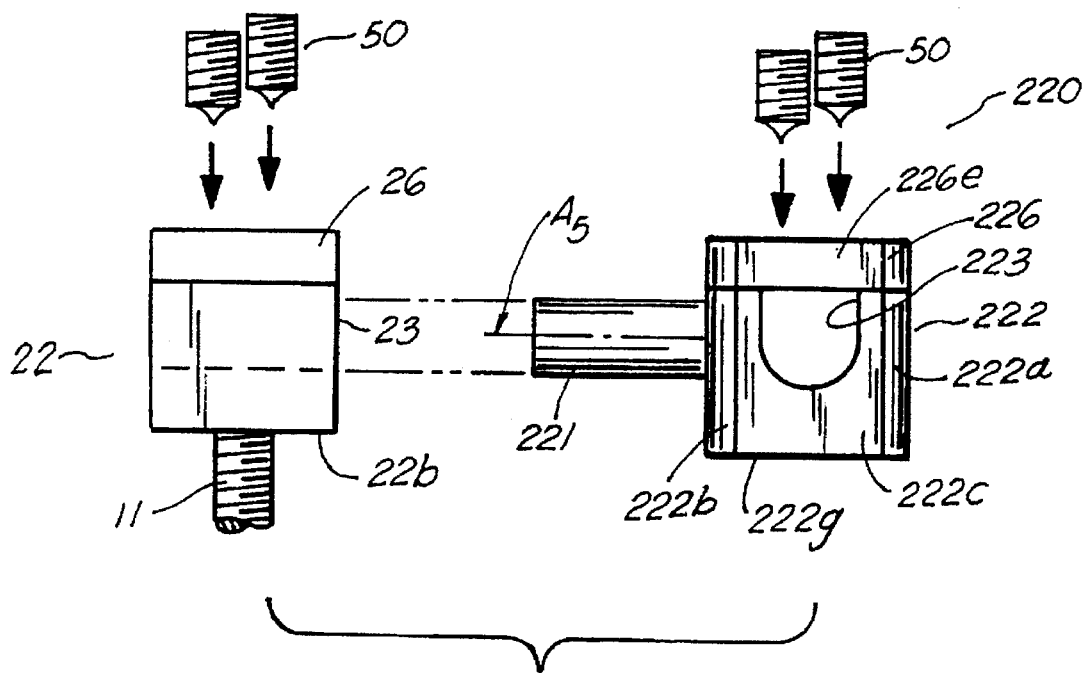
FIG. 6A is an exploded side elevation view of the screw and open head transverse extension device assembly.
Figure 6B:
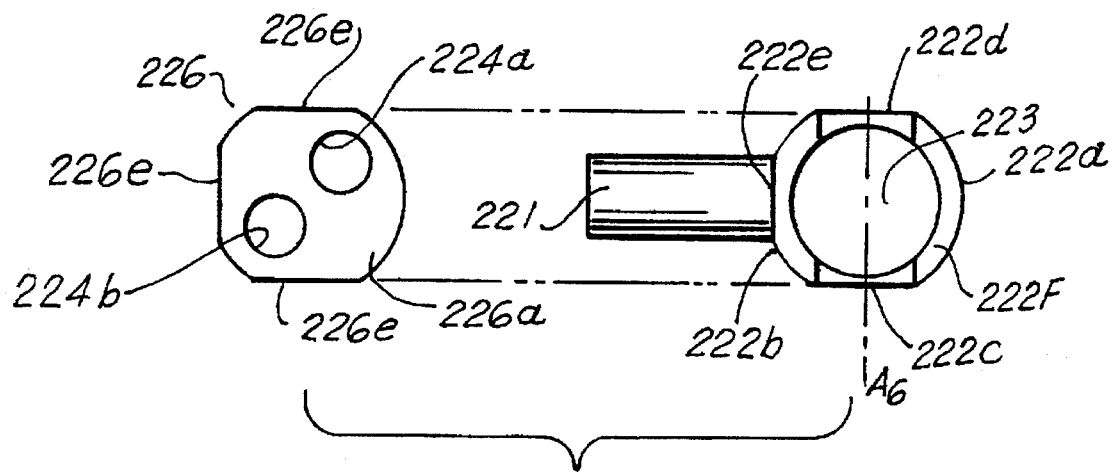
FIG. 6B is a top plan view of the transverse extension device illustrated in FIG. 6A.

Another aspect of the present invention comprises a transverse connector (220) having an open head, as shown in FIGS. 6A-B, similar to the open head design for the orthopedic fasteners described above. Thus, the head (222) comprises two parallel side walls (222a, 222b) integral with and perpendicular to a lower end (222g). In addition, one of the two side walls (222b) is integral with the longitudinal member (221). Preferably, the side wall (222b) integral with the longitudinal member (221) has a substantially flat and toughened or knurled surface (222e) (as also indicated by the shading in FIG. 6C) to minimize sliding against a similarly flat and roughened surface of the fastener head or a second transverse connector head. In addition, the connector head may comprise two U-shaped walls (222c, 222d) integral with the two parallel side walls (222a, 222b) and positioned parallel to one another. The two U-shaped walls, which are preferably substantially flat and roughened for reasons discussed above, are designed for direct contact with the head of a second transverse connector (not shown). The head further includes a transverse channel or bore (223) communicating between the two parallel side walls (222a, 222b) and U-shaped side walls, if present, and is positioned perpendicular to the longitudinal axis ($A_5$) of the longitudinal member (221).

Figure 6C:
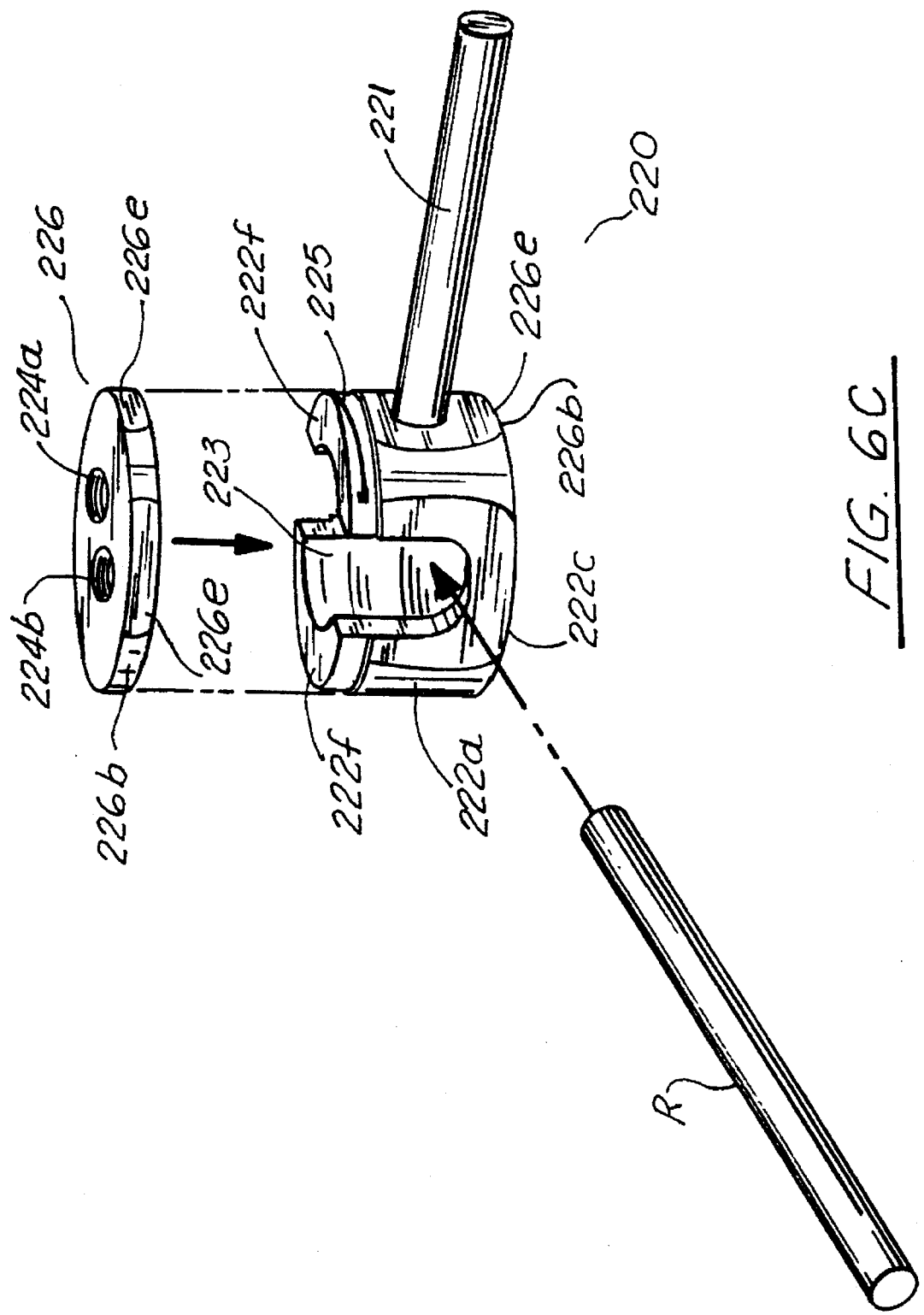
FIG. 6C is an exploded perspective view of the open head transverse extension device.

The transverse connector (220) further includes a lid (226) essentially identical to that described for the orthopedic fasteners described herein and which attaches to the upper ends (222f) of the head, as shown in FIG. 6C. The lid (226) may be designed to snap onto the upper end (222f);

however, more preferably the lid is designed for threadable engagement onto a threaded rim (225) of the connector head. Similarly, the rim (226b) of the lid is preferably of sufficient thickness such that it includes on its outer surface from one to four, preferably three, flat portions (226e) to align with the outer flat surfaces of the head. The flat portions (226e) are also preferably roughened or knurled, as indicated by the shading in FIG. 6C.

The top portion (226a) of the lid also contains a pair of holes (224a, 224b) communicating with, and perpendicular to, the longitudinal axis ($A_6$) of the channel. Preferably, the two holes (224a, 224b) are staggered and oriented such that a longitudinal member, preferably a spinal rod or another connector member, for example, when placed within the channel (223), is aligned between each of the two holes (224a, 224b). Positioned within each the two holes (224a, 224b) is the same set screw (50) described herein for the closed and open head orthopedic fasteners (10, 20) and the closed head transverse extension device (110). Because of the position of the lid, the pair of holes (224a, 224b) are positioned perpendicular to the longitudinal axis ($A_5$) of the member similar to the closed head transverse connector (110). As discussed above, this alignment of the two holes for engaging the set screws is one advantage of the present invention in that it allows the surgeon top access to the fixation system for ease of assembly during surgery.

The inventive orthopedic fasteners and transverse extension devices may be used alone, in combination with each other, or in combination with other extension devices and orthopedic fasteners. When used in combination with each other in a kit, for example, it may be desireable that the kit include a plurality of transverse extension devices of various sizes and lengths, specifically of different longitudinal member lengths, to accommodate the various distances which may extend throughout the area of fixation between the spinal rod and the fastener heads.

Figure 9B:
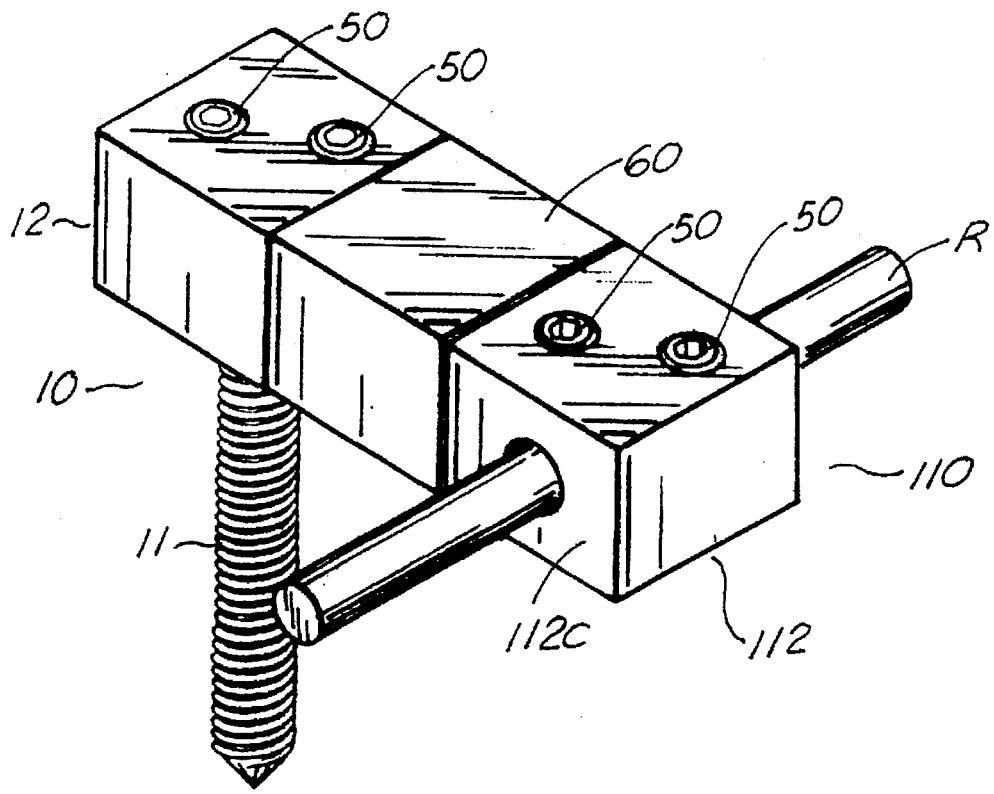
FIG. 9B is a perspective view of the assembled fixation system illustrated in FIG. 9A.
Figure 9C:
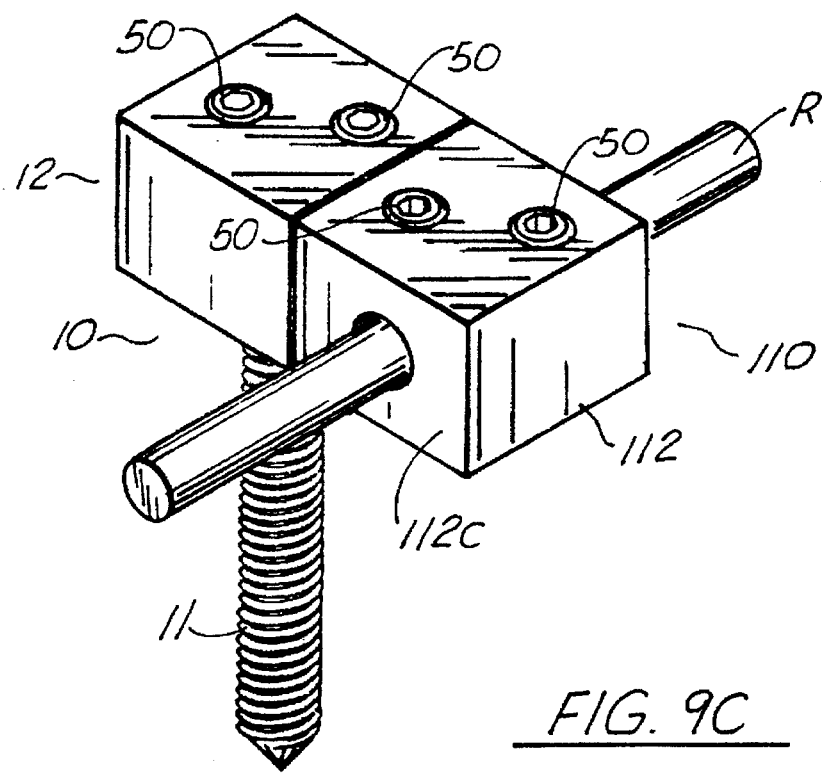
FIG. 9C is a perspective view of the assembled fixation system comprising the closed head screw and transverse extension device, set screws, and rod.

When the transverse connector is used for the purpose of minimizing rod contouring in the frontal plane, a preferred aspect of the present invention is to slide onto the longitudinal member (111) of the transverse connector a sufficient number of spacers (60), as illustrated in FIGS. 9A–B, for example. As shown in FIG. 9A, each spacer includes at least two flat, parallel sides (60a, 60b) and a transverse bore (61) communicating therethrough. The transverse bore of the spacer is configured to house the longitudinal member (111) of the transverse connector. Preferably, when the outer surfaces of the two parallel sides (60a, 60b) of the spacers are roughened or knurled (as indicated by shading in FIG. 9A) and placed in direct contact with the roughened sides of the transverse connector head (112) and the orthopedic fastener head (12), a greater frictional contact is effected, thereby minimizing any sliding therebetween to provide a more secure stabilization of the spine. In the most preferred embodiment, a sufficient number of spacers are employed to enclose the longitudinal member of the transverse connector, thereby eliminating any space between the transverse connector head and the orthopedic fastener head to increase the mechanical strength of the fastener/transverse connector assembly.

The inventive orthopedic fasteners and transverse extension devices described herein, including the inventive set screw system, are formed of materials, mainly metals and metal alloys, typically employed by those of ordinary skill in the art in the manufacture of other orthopedic implants, particularly internal orthopedic screws and hooks. Examples of suitable materials include, but are not limited to, stainless steel, titanium, and vanadium, for example. Preferably, titanium or a titanium alloy may be used. In addition, it is preferred that the spinal fixation rod used in the present invention preferably have a smooth outer surface; however, lightly textured rods may also be suitable, as long as insertion through the fastener head(s) and/or transverse connector head(s) are not too difficult.

One significant advantage of the present invention is its simplicity, both in terms of design and method of use. Both the closed head and open head embodiments, in combination with the inventive set screw system described herein, may be applied to any type of orthopedic fastener. Consequently, when used for internal rod-based spinal fixation, the screw or hook is secured to the desired vertebra by conventional methods commonly known to those of ordinary skill in the art.

Figure 13:
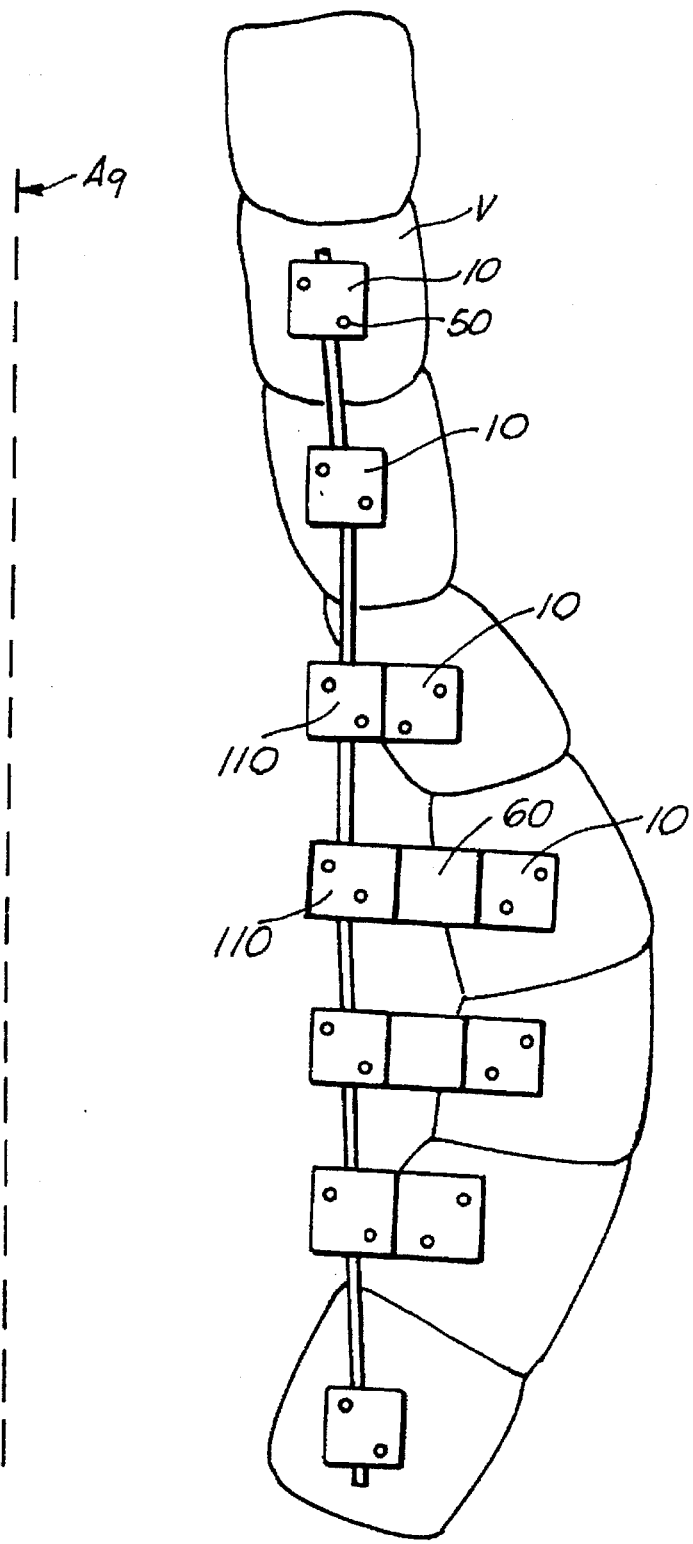
FIG. 13 is a schematic top view of the inventive fastener/transverse extension device attached to various spinal vertebrae.

As discussed above, when rod-based spinal fixation would require significant contouring of the rod in order to thread the rod through the fastener head, a transverse extension device of sufficient length may be attached to the fastener head to minimize rod contouring in the frontal plane as well as allow for essentially infinite angulation of the fastener head in the sagittal plane. To attach the transverse extension device to the fastener head wherein the fastener is already engaged within the vertebrae (V) (see FIG. 13), the fastener head is first rotated to a desired position, preferably about 90° in the case of the screw, so that the transverse bore (13) of the head is perpendicular to the longitudinal axis of the rod ($A_9$), as shown in FIG. 13. Next, the longitudinal member (111) of the transverse connector is inserted through the transverse bore (13) of the fastener head. If only angle adjustment in the sagittal plane is required, it is preferred that the length of the transverse connector member be relatively short, preferably at a minimum of about 0.50 inches, such that the surface of one of the two parallel side walls (12c) of the fastener head and the outer surface of the side wall (112b) of the transverse connector head (or spacer (60)) are in direct contact after the transverse connector has been adjusted within this plane to accommodate the spinal rod. The longitudinal member (111) of the transverse connector is then secured within the head of the fastener by tightening down the set screws (50) within the fastener head to secure the rod. If an "open head" fastener is employed, the lid (26) is secured onto the upper end (22c) of the head, afterwards the set screws are tightened down within the lid to secure the rod therein, as discussed above.

To minimize contouring of the rod in the frontal plane, a transverse connector is employed having a sufficiently long longitudinal member to accommodate the distance between the rod and the fastener head. A preferred length for the transverse connector longitudinal member is from about 0.50 inches to about 3 inches, more preferably from about 2 to about 3 inches. If there is a space between the fastener head and the transverse connector head, at least one spacer (60) may be inserted onto the connector member to accommodate the space therebetween. The head (112) of the transverse connector can be further adjusted at any angle within the sagittal plane, as discussed above, to align its transverse bore (113) with the longitudinal axis of the rod in order to minimize rod contouring in the sagittal plane, as well. Once the transverse extension connector is properly positioned, it is then secured within the fastener head by the inventive set screws (50), as described above. Similarly, once the spinal rod is positioned within the transverse connector head, it is also secured therein using the inventive locking system.

While preferably only one transverse extension device having a longitudinal member of sufficient length is desired, there may be some cases where it is desireable to connect two or more transverse connectors together to link the fastener head to the rod in order to minimize rod contouring in the frontal plane, for example. In such cases, at least three transverse extension systems would probably be needed.

The foregoing disclosure and description of the invention are illustrative and explanatory thereof, and changes in the size, shape, and materials, as well as in the details of the illustrated construction may be made without departing from the spirit of the invention.

I claim:

1. An orthopedic device suitable for securing an orthopedic longitudinal member, said device comprising:
   (a) an orthopedic fastener having an upper head and a lower engaging means integral with said head for engaging a bone, said head further comprising a transverse bore communicating therethrough for housing a longitudinal member having a substantially cylindrical surface, a lower end integral with said engaging means, and an upper end having two holes communicating with said transverse bore, wherein said two holes are oriented such that said longitudinal member is aligned between each of said two holes;
   (b) two set screws, each of said two set screws adapted for engagement within each such of said two holes, wherein each of said two set screws comprises an upper body and a lower tip having a concave outer surface configured to conform to said cylindrical surface of said longitudinal member;
   (c) wherein said longitudinal member is clamped between said lower tips of said two set screws thereby creating a three-point shear clamp grip within the transverse bore when said two set screws contact and engage said longitudinal member.

2. The device of claim 1, wherein said longitudinal member is a spinal fixation rod and said bone is a vertebra.

3. The device of claim 2, wherein said orthopedic fastener is a screw.

4. The device of claim 2, wherein said orthopedic fastener is a hook.

5. An orthopedic device suitable for securing an orthopedic longitudinal member, said device comprising:
   (a) an orthopedic fastener having an upper head and a lower engaging means integral with said head for engaging a bone, said head having a lower end integral with said engaging means, two parallel side walls integral with said lower end, an upper end positioned opposite said lower end and integral with said two parallel side walls, and an inner channel therebetween, said channel configured to receive a longitudinal member having a substantially cylindrical surface;
   (b) a lid configured to attach to the upper end of said head, wherein said lid further includes a top portion having two holes positioned therethrough such that when said lid is secured onto said upper end of said orthopedic fastener head, said longitudinal member is orientated between each of said two holes;
   (c) two set screws, each of said two set screws adapted for engagement within each of said two holes of said lid, wherein each of said two set screws comprises an upper body and a lower tip having a concave outer surface configured to conform to said cylindrical surface of said longitudinal member;
   (d) wherein said longitudinal member is clamped between said lower tips of said two set screws thereby creating a three-point shear clamp grip within the channel when said two set screws contact and engage said longitudinal member.

6. The device of claim 5, wherein said longitudinal member is a spinal fixation rod and said bone is a vertebra.

7. The device of claim 6, wherein said orthopedic fastener is a screw.

8. The device of claim 6, wherein said orthopedic fastener is a hook.

9. The device of claim 5, wherein said upper end of said orthopedic fastener head comprises a threaded rim and said lid further includes a threaded surface adapted for threadable engagement onto said threaded rim of said orthopedic fastener head.

10. The device of claim 9 wherein said orthopedic fastener is a screw.

11. The device of claim 9 wherein said orthopedic fastener is a hook.

12. A transverse extension device suitable for connecting an orthopedic fastener to a rod, said device comprising:
   (a) a transverse connector having a head and a first longitudinal member integral with said head, wherein said head further includes a transverse bore positioned perpendicular to said first longitudinal member and communicating therethrough for housing a separate second longitudinal member having a substantially cylindrical surface, and two holes communicating with said transverse bore, wherein said two holes are perpendicular to said first longitudinal member and oriented such that said second longitudinal member is aligned between each of said two holes;
   (b) two set screws, each of said two screws adapted for engagement within each of said two holes, wherein each of said two set screws comprises an upper body and a lower tip having a concave outer surface configured to conform to said cylindrical surface of said second longitudinal member;
   (c) wherein said second longitudinal member is clamped between said lower tips of said two set screws thereby creating a three-point shear clamp grip within the transverse bore when said two set screws contact and engage said second longitudinal member.

13. The device of claim 12, wherein said second longitudinal member is a spinal fixation rod.

14. The device of claim 13, wherein said orthopedic fastener is selected from the group consisting of vertebral screws and vertebral hooks.

15. A transverse extension device suitable for connecting an orthopedic fastener to a rod, said device comprising:
   (a) a transverse connector having a head and a first longitudinal member, wherein said head includes a lower end, first and second parallel side walls integral with said lower end, an upper end opposite said lower end and integral with said first and second parallel side walls, and an inner channel therebetween configured for housing a second longitudinal member having a substantially cylindrical surface, and wherein said first longitudinal member is integral with said first parallel side wall and positioned perpendicular to said first and second parallel side walls and said channel;
   (b) a lid configured to attach to the upper end of said head, wherein said lid further includes a top portion further having two holes positioned therethrough such that when said lid is secured onto said upper end of said head, said second longitudinal member is aligned between each of said two holes;
   (c) two set screws, each of said two set screws adapted for engagement within each of said two holes of said lid, wherein each of said two set screws comprises an upper body and a lower tip having a concave outer surface configured to conform to said cylindrical surface of said second longitudinal member;

(d) wherein said second longitudinal member is clamped between said lower tips of said two set screws thereby creating a three-point shear clamp grip within the channel when said two set screws contact and engage said second longitudinal member.

16. The device of claim 15, wherein said upper end of said head comprises a threaded rim and said lid further includes a threaded surface adapted for threadable engagement onto said threaded rim of said head.

17. The device of claim 16, wherein said second longitudinal member is a spinal fixation rod.

18. An orthopedic fixation device kit comprising:

(a) at least one rod;

(b) at least one orthopedic fastener selected from the group consisting of screws and hooks, said at least one orthopedic fastener having an upper head and a lower engaging means integral with said head for engaging a bone, said head further comprising a lower end integral with said engaging means, two parallel side walls integral with said lower end, a transverse bore communicating through said two parallel side walls and positioned perpendicular to said engaging means, said transverse bore adapted for housing a first longitudinal member having a substantially cylindrical surface, and an upper end having two holes communicating with, and perpendicular to, said transverse bore of said at least one fastener;

(c) at least one transverse connector having a head and a longitudinal member integral with, and extending from, a side wall of said transverse connector head, wherein said transverse connector head further includes a transverse bore positioned perpendicular to said transverse connector longitudinal member and communicating therethrough for housing a second longitudinal member, and an upper end perpendicular to said side wall and comprising at least one pair of holes extending perpendicular to, and communicating with, said connector transverse bore;

(d) at least one pair of first set screws, each of said first set screws adapted for engagement within each of said two orthopedic fastener head holes, wherein each of said two first set screws comprises an upper body and a lower tip having a concave outer surface configured to conform to said substantially cylindrical surface of said first longitudinal member; and (e) at least one pair of second set screws, each of said second set screws adapted for engagement within each of said two connector head holes, wherein each of said two second set screws comprises an upper body and a lower tip having a concave outer surface configured to conform to said substantially cylindrical surface of said second longitudinal member;

wherein said first longitudinal member and said second longitudinal member are selected from the group consisting of said at least one rod and said transverse connector longitudinal member.

19. The kit of claim 18, wherein said side wall of said transverse connector head and at least one of said two parallel side walls of said orthopedic fastener head include roughened surfaces.

20. The kit of claim 18 and further including at least one spacer adapted for housing said transverse connector longitudinal member, wherein said at least one spacer is positioned between said orthopedic fastener head and said transverse connector head.

21. The kit of claim 20, wherein said at least one spacer has a roughened inner surface and a roughened outer surface.

22. The kit of claim 18, wherein at least one of said two parallel side walls of said at least one orthopedic fastener are substantially flat, and wherein said upper end of said orthopedic fastener head is a lid configured to attach to said orthopedic fastener head to enclose said first longitudinal member within said orthopedic fastener head.

23. The kit of claim 22, wherein said side wall of said transverse connector head and at least one of said two parallel side walls of said orthopedic fastener head include roughened outer surfaces.

24. The kit of claim 22 and further including at least one spacer adapted for housing said transverse connector longitudinal member, wherein said at least one spacer is positioned between said orthopedic fastener head and said transverse connector head.

25. The kit of claim 22, wherein said at least one spacer has a roughened inner surface and a roughened outer surface.

26. The kit of claim 22, wherein said side wall of said transverse connector head is substantially flat, and wherein said upper end of said transverse connector head is a lid configured to attach to said transverse connector head to enclose said second longitudinal member within said transverse connector head.

27. The kit of claim 26, wherein said side wall of said transverse connector head and said at least one of said two parallel side walls of said orthopedic fastener head include roughened outer surfaces.

28. The kit of claim 26 and further including at least one spacer adapted for housing said transverse connector longitudinal member, wherein said at least one spacer is positioned between said orthopedic fastener head and said transverse connector head.

29. The kit of claim 26, wherein said at least one spacer has a roughened inner surface and a roughened outer surface.

30. The kit of claim 18, wherein said side wall of said transverse connector head is substantially flat and said upper end of said transverse connector head is a lid configured to attach to said transverse connector head to enclose said second longitudinal member within said transverse connector head.

31. The kit of claim 30, wherein said side wall of said transverse connector head and said at least one of said two parallel side walls of said orthopedic fastener head include roughened surfaces.

32. The kit of claim 30 and further including at least one spacer adapted for housing said transverse connector longitudinal member, wherein said at least one spacer is positioned between said orthopedic fastener head and said transverse connector head.

33. The kit of claim 30, wherein said at least one spacer has a roughened inner surface and a roughened outer surface.

34. An apparatus for securing a longitudinal member having a substantially cylindrical outer surface, said apparatus comprising:

(a) a housing component having a transverse bore for engaging said longitudinal member and at least two holes positioned perpendicular to, and communicating with, said transverse bore, wherein said at least two holes are oriented such that said longitudinal member is aligned between each of said two holes;

(b) at least two set screws, each of said at least two set screws adapted for engagement within each of said at least two holes, wherein each of said at least two set screws comprises an upper body and a lower tip having a concave outer surface configured to conform to said substantially cylindrical outer surface of said longitudinal member;

(c) wherein said longitudinal member is clamped between said lower tips of said two set screws thereby creating a three-point shear clamp grip within the transverse bore when said two set screws contact and engage said longitudinal member.

35. The apparatus of claim 34, wherein said longitudinal member is an orthopedic rod.

36. The apparatus of claim 35, wherein said orthopedic rod is a spinal fixation rod.

37. A method of spinal fixation comprising the steps of:

(a) attaching each of at least one orthopedic fastener to each of at least one vertebra, said orthopedic fastener comprising an upper head and a lower engaging means integral with said head for engaging said at least one vertebra, said head further comprising a transverse bore and a first pair of holes communicating with said orthopedic fastener transverse bore, each of said first pair of holes adapted for engaging a first and second set screw respectively;

(b) attaching a first transverse connector to at least one of said at least one orthopedic fastener, said first transverse connector comprising a head and a longitudinal member having a substantially cylindrical surface, said transverse connector longitudinal member integral with, and extending from, a side wall of said transverse connector head, wherein said transverse connector head further includes a transverse bore and a second pair of holes communicating with said connector transverse bore, each of said second pair of holes adapted for engaging a third and fourth set screw respectively;

(c) locking said first transverse connector within said transverse bore of said at least one orthopedic fastener by engaging each of said first and second set screws within each of said first pair of holes;

(d) inserting a spinal fixation rod through said transverse bore of said first transverse connector attached to each of said at least one orthopedic fastener, said rod having a substantially cylindrical surface; and (e) locking said spinal fixation rod within said transverse bore of said first transverse connector by engaging each of said third and fourth set screws within each of said second pair of holes; and wherein said each of said first and second set screws comprises an upper body and a lower tip having a concave outer surface configured to conform to said substantially cylindrical surface of said longitudinal member of said transverse connector, and wherein each of said third and fourth set screws comprises an upper body and a lower tip having a concave outer surface configured to conform to said substantially cylindrical surface of said spinal fixation rod.

38. The method of claim 37, further including the steps of:

(f) attaching a second transverse connector to said first transverse connector;

(g) inserting said spinal fixation rod through a head of said second transverse connector; and (h) locking said spinal fixation rod within said second transverse connector.

* * * * *